(12) United States Patent
Jin et al.

(10) Patent No.: US 10,799,445 B2
(45) Date of Patent: Oct. 13, 2020

(54) MOISTURIZING COSMETIC COMPOSITION

(71) Applicant: Yang Sheng Tang (Shanghai) Cosmetic R&D Co., Ltd., Shanghai (CN)

(72) Inventors: Xin Jin, Shanghai (CN); Shizhi Zhao, Shanghai (CN); Loucheng Zhao, Shangai (CN)

(73) Assignee: Yang Sheng Tang (Shanghai) Cosmetic R&D Co., Ltd., Shanghai (CN)

( * ) Notice: Subject to any disclaimer, the term of this patent is extended or adjusted under 35 U.S.C. 154(b) by 0 days.

(21) Appl. No.: 16/340,650

(22) PCT Filed: Mar. 7, 2018

(86) PCT No.: PCT/CN2018/078206
§ 371 (c)(1),
(2) Date: Apr. 9, 2019

(87) PCT Pub. No.: WO2018/196481
PCT Pub. Date: Nov. 1, 2018

(65) Prior Publication Data
US 2020/0046631 A1    Feb. 13, 2020

(30) Foreign Application Priority Data

Apr. 27, 2017 (CN) .......................... 2017 1 0290345

(51) Int. Cl.

| | | |
|---|---|---|
| A61K 36/88 | (2006.01) | |
| A61K 8/9789 | (2017.01) | |
| A61K 8/34 | (2006.01) | |
| A61K 8/365 | (2006.01) | |
| A61K 8/37 | (2006.01) | |
| A61K 8/44 | (2006.01) | |
| A61K 8/73 | (2006.01) | |
| A61Q 19/00 | (2006.01) | |

(52) U.S. Cl.
CPC ............ *A61K 8/9789* (2017.08); *A61K 8/345* (2013.01); *A61K 8/365* (2013.01); *A61K 8/37* (2013.01); *A61K 8/44* (2013.01); *A61K 8/735* (2013.01); *A61Q 19/007* (2013.01); *A61K 2800/31* (2013.01)

(58) Field of Classification Search
None
See application file for complete search history.

(56) References Cited

U.S. PATENT DOCUMENTS

| | | | |
|---|---|---|---|
| 5,750,578 A | 5/1998 | Carlson et al. | |
| 6,572,868 B1 | 6/2003 | Cope | |
| 6,642,217 B2 | 11/2003 | Krasutsky et al. | |
| 7,482,383 B2 | 1/2009 | Scheffler | |
| 8,367,818 B2 | 2/2013 | Yoshida et al. | |
| 9,827,214 B2 | 11/2017 | Scheffler | |
| 2006/0093571 A1 | 5/2006 | Glinski | |
| 2009/0312282 A1 | 12/2009 | Yoshida et al. | |
| 2012/0028916 A1 | 2/2012 | Fournial et al. | |

FOREIGN PATENT DOCUMENTS

| | | | |
|---|---|---|---|
| CN | 1426305 A | | 6/2003 |
| CN | 1839783 A | | 10/2006 |
| CN | 101959439 A | | 1/2011 |
| CN | 102093458 A | | 6/2011 |
| CN | 102665723 A | | 9/2012 |
| CN | 102683701 A | | 1/2013 |
| CN | 103565705 A | | 2/2014 |
| CN | 103705425 A | | 4/2014 |
| CN | 105662940 A | | 6/2016 |
| CN | 105687044 A | | 6/2016 |
| CN | 105708757 A | | 6/2016 |
| CN | 105769707 A | | 7/2016 |
| CN | 105878119 A | | 8/2016 |
| CN | 106109265 A | | 11/2016 |
| CN | 106137865 A | | 11/2016 |
| CN | 106361653 A | | 2/2017 |
| CN | 106420498 A | | 2/2017 |
| CN | 106420532 | * | 2/2017 |
| CN | 106420532 A | | 2/2017 |
| CN | 107019660 | * | 8/2017 |
| CN | 107049865 A | | 8/2017 |
| CN | 107184411 A | | 9/2017 |
| CN | 107019660 B | | 5/2018 |
| CN | 108771633 A | | 11/2018 |
| EP | 2 012 795 A2 | | 1/2009 |
| JP | 9-291013 A | | 11/1997 |
| JP | H-10-152444 A | | 6/1998 |

(Continued)

OTHER PUBLICATIONS

International Search Report and Written Opinion of the International Searching Authority dated Jun. 5, 2018, for PCT Application No. PCT/CN2018/078206, filed on Mar. 7, 2018, 8 pages (with English translation).
International Search Report and Written Opinion of the International Searching Authority dated Jun. 7, 2018; for PCT Application No. PCT/CN2018/078208, filed on Mar. 7, 2018, 13 pages (with English translation).
Jiang, Zhonghai (2002). Study on the Birch Juice in Heilongjiang, Science and Technology of Food industry, pp. 62-63 (with English translation).
Ordinary Biochemical Course (2008). ISBN 978-7-122-01997-4, http://www.cip.com.cn, p. 161, 4 total pages (with English translation).
Practical Cosmetic Drugs (2016). ISBN 978-7-5680-2113-5, http://www.hustp.com, p. 32, 10 total pages (with English translation).

(Continued)

*Primary Examiner* — Ralph J Gitomer

(57) ABSTRACT

The invention relates to a moisturizing cosmetic composition comprising: (A) 30-99 wt % of birch sap, (B) 0.001-5 wt % of hydrolyzed sodium hyaluronate, and (C) optionally, ingredients commonly used in skincare cosmetics, wherein the moisturizing cosmetic composition of the invention does not comprise water typically added as a separate component.

16 Claims, 1 Drawing Sheet

(56) References Cited

FOREIGN PATENT DOCUMENTS

| | | |
|---|---|---|
| JP | H-10-279466 A | 10/1998 |
| JP | 3072027 U | 7/2000 |
| JP | 2002-029979 A | 1/2002 |
| JP | 2003-321323 A | 11/2003 |
| JP | 2006-232693 A | 9/2006 |
| JP | 2007-217325 A | 8/2007 |
| JP | 2007-320921 A | 12/2007 |
| JP | 2008-088109 A | 4/2008 |
| JP | 2009-013100 A | 1/2009 |
| JP | 2010-143893 A | 7/2010 |
| KR | 10-2003-0067554 A | 8/2003 |
| KR | 10-2008-0097477 A | 11/2008 |
| KR | 101682123 B1 | 12/2016 |
| RU | 2 411 934 C1 | 2/2011 |
| WO | WO-00/03749 A2 | 1/2000 |
| WO | WO-00/03749 A3 | 1/2000 |
| WO | WO-03/024418 A2 | 3/2003 |
| WO | WO-03/024418 A3 | 3/2003 |
| WO | WO-2005/047304 A2 | 5/2005 |
| WO | WO-2005/047304 A3 | 5/2005 |
| WO | WO-2007/099830 A1 | 9/2007 |
| WO | WO-2007/121352 A2 | 10/2007 |
| WO | WO-2007/121352 A3 | 10/2007 |
| WO | WO-2011/107522 A2 | 9/2011 |
| WO | WO-2011/107522 A3 | 9/2011 |
| WO | WO-2018/017576 A1 | 1/2018 |
| WO | WO-2018/196482 A1 | 11/2018 |

OTHER PUBLICATIONS

Chinese Office Action dated Apr. 2, 2020, for Chinese Patent Application No. 201810863822.0, 11 total pages (with English translation).
Database WPI (2017). "Birch tree liquid cosmetic lotion for removing acne and freckles on people's face, comprises preset amount of red raspberry fruit distillate, potassium sorbate, vitamin C, hyaluronic acid, lysozyme, jasmine flavor and birch tree liquid", Week 201711, Mar. 1, 2017, Thomson Scientific, London, GB; AN 2017-071785, XP002798795, 2 total pages.
Database GNPD (2010). Mintel, Oct. 29, 2010, Fuwarich Lotion, Humalabo Co., XP055688005, retrieved from www.gnpd.com Database accession No. 1427977, 4 total pages.
Extended European Search Report dated May 6, 2020, for EP Application No. 18 792 071.5, 9 total pages.
Madara Cosmetics, Latvia, Advanced Anti-Aging Day Cream, Mintel GNPD (2013). ID No. 2064631, 4 total pages.
Ohtera, A. (2005). Fragrance Journal, vol. 33, No. 10, pp. 89-94 (English translation of abstract).
Extended European Search Report dated Jul. 25, 2019, for EP Application No. 18 790 847.0, 8 total pages.
Hokkaido (2009). Moisturing Raw Material, Fragrance Journal, pp. 121-122 (with English translation).

* cited by examiner

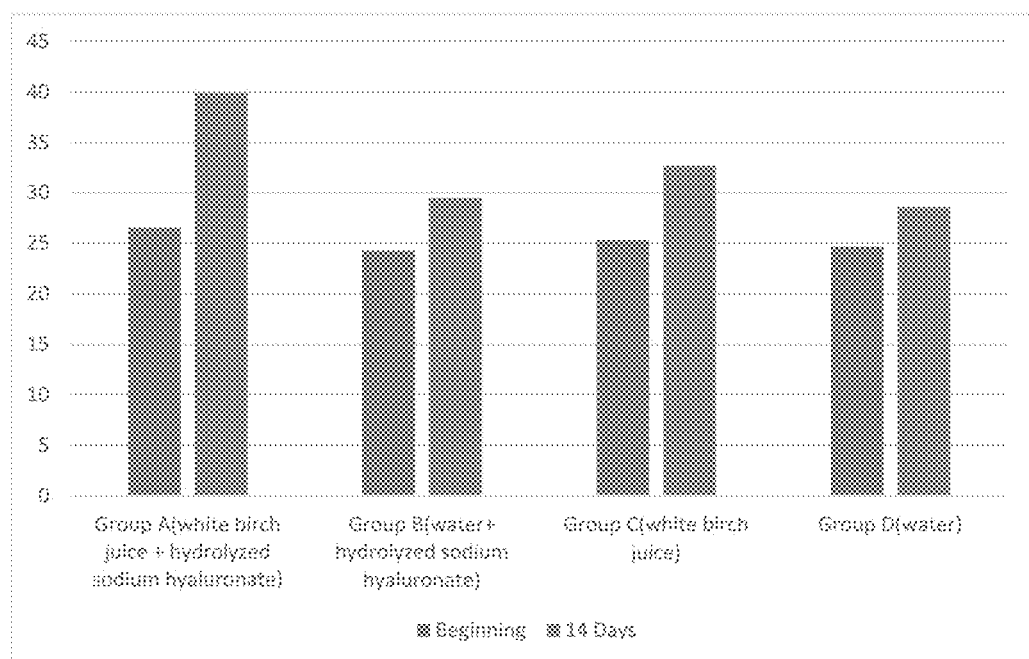

MOISTURIZING COSMETIC COMPOSITION

RELATED APPLICATIONS

This application is a U.S. National Phase application, filed under 35 U.S.C. § 371(c), of International Application No. PCT/CN2018/078206, filed Mar. 7, 2018, which claims priority to, and the benefit of, Chinese Patent Application No. 201710290345.9, filed Apr. 27, 2017, each of which is incorporated by reference herein in its entirety for all purposes.

TECHNICAL FIELD

The invention relates to a moisturizing cosmetic composition comprising birch sap, hydrolyzed sodium hyaluronate, and optional ingredients commonly used in skincare cosmetics, but no water typically added as a separate component.

BACKGROUND ART

Moisturizing is very important for maintaining skin health. The traditional water-soluble moisturizing products on the market are still mainly composed of the ingredients such as polyols and polymers, these ingredients can absorb the moisture in the air, however, when the climate is dry, they also absorb the moisture from the skin, and thus the moisturization all the time is difficult. Also, a large amount of minerals and trace elements beneficial to skin moisturization still cannot be added to ordinary cosmetics.

Skin moisturizing is mainly achieved by supplying moisture to the stratum corneum. However, the most important way to transport water to the stratum corneum is through aquaporin. The opening of aquaporin is controlled and regulated by the ionic strength of minerals and the ions of calcium, magnesium, potassium and the like, so an environment with certain ionic strength of minerals and rich in the ions of calcium, magnesium, potassium and the like will facilitate water transport across the membrane to the stratum corneum, thereby increasing the moisture content of the skin. Birch sap is rich in natural minerals, which makes the above theory become possible and thus can completely replace the water in cosmetics.

All the commercially available products comprising birch sap and hydrolyzed sodium hyaluronate comprise water, the presence of water will change the concentration of mineral ions in birch sap, thereby affecting the transport of water in birch sap and hydrolyzed sodium hyaluronate across the membrane.

Therefore, the invention attempts to use birch sap instead of water to promote the absorption of the above substances by the stratum corneum. The inventors have found through experiments that birch sap significantly promotes the transdermal absorption of hydrolyzed sodium hyaluronate, thereby achieving improved moisturizing and other skincare efficacy.

DESCRIPTION OF THE DRAWINGS

FIG. 1 is a graph showing the moisturizing effects of a toner A of the invention and controls B-D.

DETAILED DESCRIPTION OF THE INVENTION

An object of the invention is to provide a moisturizing cosmetic composition comprising (A) 30-99 wt % of birch sap, (B) 0.001-5 wt % of hydrolyzed sodium hyaluronate, and (C) optionally, ingredients commonly used in skincare cosmetics, wherein the moisturizing cosmetic composition according to the invention does not comprise water typically added as a separate component.

The cosmetic composition according to the invention can significantly improve moisturizing and skincare efficacy.

The skincare cosmetic composition of the invention does not comprise any added water, but does not exclude the inherent moisture in the birch sap or a small or trace amount of water inevitably introduced from other ingredients.

In a preferred embodiment, the moisturizing cosmetic composition according to the invention does not comprise a chelating agent such as EDTA salt, sodium polyphosphate, sodium metaphosphate or gluconic acid and the like.

The invention further relates to a method for increasing the transdermal absorption of hydrolyzed sodium hyaluronate, comprising adding birch sap to a moisturizing cosmetic composition comprising hydrolyzed sodium hyaluronate and no added water. The method can significantly increase the transdermal absorption of hydrolyzed sodium hyaluronate, thereby achieving significantly improved moisturizing effect.

The invention also relates to use of a combination of birch sap and hydrolyzed sodium hyaluronate in moisturizing cosmetic composition comprising add.

The birch tree involved in the invention belongs to *Betula betulaceae*, which may be the three varieties of *Betula alba*, *Betula pendula* and *Betula platyphylla*.

The collection time of the birch sap as component (A) is from the time of snow beginning to melt to the time of tree foliation. During the collection, a small hole is drilled in the birch trunk of 40-60 cm high from the ground, and a liquid guiding device is introduced. After the birch sap is collected and filtered, it is further sterilized by conventional methods to obtain a colorless, transparent, fragrant and nutritious birch sap without precipitates or impurities. The collected birch sap is not subjected to irradiation and not added with a preservative to maximize the preservation of the nutrients of the birch sap. The birch sap is commercially available and used as it is, for example, it can be commercially available from Daxinganling Chaoyue Wild Berry Development Co., Ltd.

The moisturizing cosmetic composition according to the invention may comprise 30-99 wt %, preferably 50-95 wt %, more preferably 70-90 wt % of birch sap, based on the total weight of the composition.

The hydrolyzed sodium hyaluronate as component (B) is molecular fragments prepared by enzyme digesting sodium hyaluronate, which have a very small molecular weight of typically 1-10 KDa, preferably 3-8 KDa, more preferably 5-7 KDa. The hydrolyzed sodium hyaluronate can quickly penetrate into the stratum corneum to provide a long-lasting skin moisturizing effect. The hydrolyzed sodium hyaluronate can be prepared by a method known in the art, for example, firstly preparing sodium hyaluronate from a plant-derived medium (peptone, glucose, etc.) by a fermentation method, and then preparing hydrolyzed sodium hyaluronate by an enzyme digestion. Hydrolyzed sodium hyaluronate is also commercially available, for example, it can be commercially available from Huaxi Furida Biomedical Co., Ltd., which has a molecular weight of ≤10 KDa.

The hydrolyzed sodium hyaluronate used in the invention has the characteristics of small molecular weight and rapid penetration, thus can directly penetrate into the dermis to achieve deep water retention, hydration, promote cell proliferation and stimulate collagen generation. Hyaluronic acid can be used in an acidic formulation, but it is easy to combine with the cations in the formulation, and thereby is instable; ordinary sodium hyaluronate can only achieve surface layer moisturizing effect on the skin surface. In addition, hydrolyzed sodium hyaluronate and sodium hyaluronate have different skin sensations: hydrolyzed sodium hyaluronate can penetrate quickly, so the skin feels fresh and non-sticky, and the amount added in the composition can also be relatively large; while ordinary sodium hyaluronate uses its own network structure to absorb water on the surface of the skin, and a small amount of it can moisturize and also bring a sense of smoothness, however, if the amount is large, the skin feels sticky.

The moisturizing cosmetic composition according to the invention may comprise 0.001-5 wt %, preferably 0.01-1 wt %, more preferably 0.1-0.5 wt % of hydrolyzed sodium hyaluronate, based on the total weight of the composition.

The moisturizing cosmetic composition according to the invention also optionally comprises, as component (C), ingredients commonly used in skincare cosmetics, including a vehicle, an active ingredient, a surfactant and an excipient. Component (C) is known in the art, and those skilled in the art can specifically select the type and amount as needed. Generally, component (C) is present in the composition of the invention in an amount of 0-65 wt %, based on the total weight of the composition.

The vehicle is, for example, a diluent, a dispersant or a carrier. All of these vehicles are known in the art, and those skilled in the art can specifically select the type and amount as needed. For example, the vehicle includes, but is not limited to, ethanol, dipropylene glycol, butylene glycol, and the like. Typically, the vehicle is present in the composition of the invention in an amount of 0.5-20% based on the total weight of component (C).

The active ingredients include, for example, an emollient, a moisturizer, a skin conditioner, and the like. All of these active ingredients are known in the art, and those skilled in the art can specifically select the type and amount as needed.

For example, the emollient includes, but is not limited to, one or more of olive oil, macadamia nut oil, sweet almond oil, grape seed oil, avocado oil, corn oil, sesame oil, soybean oil, peanut oil, meadowfoam seed oil, safflower seed oil, rose canine fruit oil, *Arganla spinosa* kernel oil, *Simmondsia chinensis* seed oil, sunflower seed oil, *Mauritia flexuosa* fruit oil, squalane, ethylhexyl palmitate, isopropyl myristate, hydrogenated polyisobutylene, isocetane, isododecane, diethylhexyl carbonate, dioctyl carbonate, isopropyl lauroyl sarcosinate, isononyl isononanoate, hydrogenated polydecene, triethylnexanoin, cetyl ethylhexanoate, bis-ethoxydiglycol cyclohexane 1,4-dicarboxylate, caprylic/capric triglyceride, oleyl erucate, octyldodecanol myristate, octyldodecanol, polydimethylsiloxane, octyl polymethylsiloxane, cetyl dimethicone, cyclopentadimethylsiloxane, and so on. The solid emollient according to the invention includes, but is not limited to, one or more of cetyl alcohol, stearyl alcohol, cetearyl alcohol, behenyl alcohol, squalyl alcohol, lauric acid, myristic acid, palmitic acid, stearic acid, beeswax, candelilla wax, carnauba wax, lanolin, ozokerite, jojoba seed wax, paraffin wax, microcrystalline wax, hydrogenated rice bran wax, hydrogenated cocoglycerides, glyceryl behenate/eicosadioate, myristyl myristate, bis-diglyceryl polyacyladipate-2, *Butyrospermum parkii* (shea butter), *Astrocaryum murumuru* seed butter. The content of the emollient in the composition is known in the art. Typically, the emollient is present in the composition of the invention in an amount of 1-50 wt % based on the total weight of the component (C).

For example, the moisturizer includes, but is not limited to, one or more of glycerin, diglycerin, propylene glycol, 1,3-propanediol, 1,2-pentanediol, polyethylene glycol-8, polyethylene glycol-32, methyl gluceth-10, methyl gluceth-20, PEG/PPG-17/6 copolymer, glycereth-7, glycereth-26, glyceryl glucoside, PPG-10 methyl glucose ether, PPG-20 methyl glucose ether, PEG/PPG/polybutylene glycol-8/5/3 glycerin, sucrose, trehalose, rhamnose, mannose, raffinose, betaine, erythritol, xylitol, urea, glycereth-5 lactate, sodium hyaluronate, sodium polyglutamate, hydrolyzed sclerotium gum, pululan, tremellam, tamarindus indica seed polysaccharide, and so on. The content of the moisturizer in the composition is known in the art. Typically, the moisturizer is present in the composition of the invention in an amount of 1-30 wt % based on the total weight of the component (C).

The skin conditioner may include active ingredients for moisturizing, anti-wrinkle, anti-freckle, anti-acne, oil control, etc., including but not limited to one or more of kojic acid, ascorbic acid, ascorbyl glucoside, arbutin, tranexamic acid, nicotinamide, phytosterols, phytosteryl/behenyl/octyldodecyl lauroyl glutamate, phenylethyl resorcinol, turmeric extract, birch bark extract, ceramide 2, ceramide 3, acetyl phytosphingosine, resveratrol, *Pterocarpus marsupium* bark extract, *Plectranthus barbatus* root extract, pepper seed extract, ubiquinone, cholesterol, cholesterol stearate, ascorbyl dipalmitate, Tocopherol (vitamin E), tocopheryl acetate, alpha-bisabolol, ascorbyl tetraisopalmitate, pyridoxine dicaprylate, pyridoxine dipalmitate, retinyl palmitate, phytosteryl/octyldodecyl lauroyl glutamate, bis-behenyl/isostearyl/phytosteryl dimer dilinoleyl dilinoleate, phytosteryl macadamiate, peptides, plant extracts and the like. The content of the skin conditioner in the composition is known in the art. Typically, the skin conditioner is present in the composition of the invention in an amount of 0.01-50 wt % based on the total weight of the component (C).

The excipient includes, but is not limited to, a surfactant, an emulsifier, a thickener, a preservative, a perfume, a pH regulator, and the like. All of these excipient ingredients are known in the art, and those skilled in the art can specifically select the type and amount as needed.

The surfactant is used for reducing the surface tension of the interface to achieve the purpose of cleaning, emulsifying and stabilizing the system. It can be any type of surfactant commonly used in cosmetics, and those skilled in the art can select its type and amount as needed. For example, the surfactant may include, but is not limited to, soap of fatty acids (e.g., sodium laurate, sodium palmitate, etc.), higher alkyl sulfates (e.g., sodium lauryl sulfate, etc.), alkyl ether sulfates (e.g., PEG-lauryl sulfate triethanolamine, PEG-sodium lauryl sulfate, etc.), N-acylsarcosine (e.g., sodium lauroyl sarcosinate, etc.), a higher fatty acid amide sulfonate (e.g., sodium laurylmethyltaurate, etc.), alkylbenzenesulfonate, higher fatty acid ester sulfates (e.g., hardened coconut oil fatty acid glycerine sodium sulfate, etc.), N-acyl glutamate, α-olefin sulfonate, lauryl dimethylamino acetic acid betaine, alkyl betaines, amido betaines, sulfobetaines, sorbitan fatty acid esters (e.g., sorbitan monooleate, sorbitan monoisostearate, sorbitan monolaurate, sorbitan monopalmitate, sorbitan monostearate, sorbitan sesquioleate), glycerol polyglycerol fatty acid esters (e.g., monoerucin, glyceryl sesquioleate, glyceryl monostearate, glyceryl monostearyl malate, etc.), propylene glycol fatty acid esters (e.g., propylene glycol monostearate, etc.), hydrogenated castor oil derivatives, glyceryl alkyl ethers, etc., PEG sorbitan fatty acid esters (e.g., PEG-sorbitan monolaurate, PEG-sorbitan monooleate, PEG-sorbitan monostearate, etc.), PEG-glyceryl fatty acid esters (e.g., PEG-glyceryl monostearate, PEG-glyceryl monoisostearate, etc.), PEG-fatty acid esters (e.g., PEG-distearate, ethylene glycol distearate, etc.), PEG-alkyl ethers (e.g., PEG-2-octyldodecyl ethers, etc., PEG-castor oil hardened castor oil derivatives (e.g., PEG-hydrogenated castor oil, PEG-hydrogenated castor oil monoisostearate, PEG-hardened castor oil maleate, etc.), sucrose fatty acid esters, etc. The content of the surfactant in the composition is known in the art. Typically, the surfactant is present in the composition of the invention in an amount of 1-50 wt % based on the total weight of the component (C).

For example, the emulsifier includes, but is not limited to, one or more of cetearyl olivate, sorbitan olivate, polysorbate-60, polysorbate-80, methyl glucose sesquistearate, PEG-20 methyl glucose sesquistearate, PEG-40 hydrogenated castor oil, PPG-26-buteth-26, PEG-4 polyglyceryl-2 stearate, PEG-60 Hydrogenated castor oil, steareth-2, steareth-21, PPG-13-decyltetradeceth-24, cetearyl glucoside, PEG-100 stearate, glyceryl stearate, glyceryl stearate SE, coco glucoside, ceteareth-25, PEG-40 stearate, polyglyceryl-3 methyl glucose distearate, glyceryl stearate citrate, polyglyceryl-10 stearate, polyglyceryl-10 myristate, polyglyceryl-10 dioleate, polyglyceryl-10 laurate, polyglyceryl-10 isostearate, polyglyceryl-10 oleate, polyglyceryl-10 diisostearate, polyglyceryl-6 laurate, polyglyceryl-6 myristate, sucrose stearate, sucrose polystearate, etc. The content of the emulsifier in the composition is known in the art. Typically, the emulsifier is present in the composition of the invention in an amount of 0.5-10 wt % based on the total weight of the component (C).

For example, the thickener includes, but is not limited to, one or more of high molecular polymers such as carbomers, acrylates and derivatives thereof, xanthan gum, gum arabic, polyethylene glycol-14M, polyethylene glycol-90M, succinyl polysaccharides, hydroxyethyl cellulose, hydroxypropyl cellulose, and hydroxypropyl methyl cellulose. The content of the thickener in the composition is known in the art. Typically, the thickener is present in the composition of the invention in an amount of 0.1-10 wt % based on the total weight of the component (C).

For example, the preservative includes, but is not limited to, one or more of methyl hydroxybenzoate, propyl hydroxybenzoate, phenoxyethanol, benzyl alcohol, phenylethanol, bis(hydroxymethyl)imidazolidinyl urea, potassium sorbate, sodium benzoate, chlorophenesin, sodium dehydroacetate, etc. The content of the preservative in the composition is known in the art. Typically, the preservative is present in the composition of the invention in an amount of 0.01-2 wt % based on the total weight of the component (C).

The pH regulator includes, but is not limited to, arginine, citric acid, sodium citrate, sodium hydroxide, potassium hydroxide, etc.

The moisturizing cosmetic composition of the invention can be prepared by any suitable method known in the art. For example, it can be prepared by a container commonly used in the field of cosmetics, such as a dissolution tank, an emulsification pot, a disperser, a transfer pump or the like. In the preparation, water-soluble substances are introduced into an aqueous phase dissolution tank, and oil-soluble substances are introduced into an oil phase dissolution kettle, and the two tanks are heated to about 80° C., respectively; for agglomerated raw materials, they can be pre-dispersed by a disperser. After the dissolution is completed, the oil phase and the aqueous phase are transferred into an emulsification pot, and homogenized and emulsified for about 5-15 mins. After the emulsification is completed, the temperature of the bulk is reduced to room temperature, optionally a fragrance, a preservative and the like are added, and the pH of the product is adjusted as needed. The relevant tests are done before the product is packaged and shipped. The above preparation methods can be revised or adjusted according to the product form requirement, and various product forms such as lotion, ointment, cream, or gel can be prepared as needed.

In a preferred embodiment, the invention provides a moisturizing composition having following formulation, preferably a toner, which exhibits an excellent moisturizing and other skincare efficacy.

| Ingredients | Content (wt. %) |
|---|---|
| BETULA ALBA sap | 70-90 |
| Methyl hydroxybenzoate | 0.05-0.4 |
| Hydrolyzed sodium hyaluronate | 0.1-0.5 |
| Pentanediol | 1-5 |
| Glycerol | 1-10 |
| Dipropylene glycol | 0.5-5 |
| Butanediol | 1-10 |
| Citric acid | 0.01-0.5 |
| Arginine | 0.05-1 |

EXAMPLES

The invention is further illustrated by the following examples and comparative examples, but it should be understood that these examples and comparative examples are for the purpose of more detailed description and are not intended to limit the invention in any way.

Example 1: Transdermal Absorption of Hydrolyzed Sodium Hyaluronate in Different Systems In this example, the transdermal absorptions of hydrolyzed sodium hyaluronate in aqueous and non-aqueous systems are tested and compared. The specific test formulations are shown in Table 1.

TABLE 1

|  | Formulation A | Formulation B |
|---|---|---|
| Water | 0 | 99.5 |
| BETULA ALBA sap | 99.5 | 0 |
| hydrolyzed sodium hyaluronate | 0.5 | 0.5 |

Test method: "reconstructed human epidermis" obtained by culturing "human keratinocytes" is used, and there is a maintenance medium on the bottom side of the reconstructed human epidermis. According to the above test formulations, the hydrolyzed sodium hyaluronate is prepared into a 0.5% solution using Betula alba sap or water, and 32 ul/cm$^2$ of the solution is applied onto the epidermis of the skin model, respectively, and the detection is done after 8 hours contact. 3 Parallels are done for per point. The skin tissue is washed with phosphate buffer before detection, homogenated, and the amount of hydrolyzed sodium hyaluronate absorbed by the tissue is detected by ELISA method. The test results are shown in Table 2.

TABLE 2

| Samples | Transdermal absorption (ng) (average ± standard deviation) | Transdermal absorption % |
|---|---|---|
| Total application amount | 80000 | — |
| Formulation A | 29587.9 ± 1051.2 | 36.98% |
| Formulation B | 22368.7 ± 296.3 | 27.96% |

The above results show that the transdermal absorption of hydrolyzed sodium hyaluronate is significantly improved in the system comprising *Betula alba* sap but no added water, as compared with the aqueous system.

Example 2: The Toner of the Invention Vs. The Control Toner Composition

The formulations of the toner compositions are shown in Table 3.

TABLE 3

| | Toner A the invention | Toner B Control | Toner C Control | Toner D Control |
|---|---|---|---|---|
| Water | 0 | 90.1 | 0 | 90.6 |
| BETULA ALBA sap | 90.1 | 0 | 90.6 | 0 |
| Methyl hydroxybenzoate | 0.15 | 0.15 | 0.15 | 0.15 |
| Citric acid | 0.1 | 0.1 | 0.1 | 0.1 |
| Xanthan gum | 0.1 | 0.1 | 0.1 | 0.1 |
| Hydrolyzed sodium hyaluronate | 0.5 | 0.5 | 0 | 0 |
| Glycerol | 3.55 | 3.55 | 3.55 | 3.55 |
| Butanediol | 4 | 4 | 4 | 4 |
| Methyl gluceth-20 | 1 | 1 | 1 | 1 |
| Arginine | 0.2 | 0.2 | 0.2 | 0.2 |
| Phenoxyethanol | 0.3 | 0.3 | 0.3 | 0.3 |

The toner compositions are prepared as follows:
1. Methyl hydroxybenzoate and phenoxyethanol are mixed and heated to 80° C., stirred to dissolve uniformly.
2. Xanthan gum, hydrolyzed sodium hyaluronate and butanediol are mixed uniformly.
3. *Betula alba* sap (or water) is heated to 80° C., and citric acid, glycerol, methyl gluceth-20 are added in sequence, stirred uniformly, and then the mixtures obtained in steps 1 and 2 are added.
4. The resultant is cooled down to 40° C., arginine is added to adjust the pH, and discharged.

The compositions prepared above are used in the experiments to test the moisturizing effect. Test methods are as follows: The test is carried out by a MoistureMeter SC skin surface moisture content detector available from Delfin. Approximately 0.02 grams of each composition sample is applied to the previously marked square area of volunteer's arm once every morning and night, and the sample is evenly spread onto the area. The moisture contents of the skin epidermis before application of the sample (reference) and at 14 days after application of the sample are measured by an instrument, and each area is tested repeatedly for three times, and the test results are averaged. The test results are shown in FIG. 1.

The results in FIG. 1 showed that after continuous application for 14 days, the toner A of the invention can improve the moisturizing performance of the skin by 150% or more, the control toner B can improve the moisturizing performance of the skin by 121%, the control toner C can improve the moisturizing performance of the skin by 128%, and the control toner D can improve the moisturizing performance of the skin by 115%. Therefore, the toner composition A of the invention has a better moisturizing effect than the control toner compositions B-D.

Example 3: Toner

The formulation of the toner is shown in Table 4.

TABLE 4

| | Proportion (%) |
|---|---|
| BETULA ALBA sap | 85.45 |
| Methyl hydroxybenzoate | 0.15 |
| Hydrolyzed sodium hyaluronate | 0.2 |
| Pentanediol | 3 |
| Glycerol | 5 |
| Dipropylene glycol | 2 |
| Butanediol | 4 |
| Citric acid | 0.1 |
| Arginine | 0.2 |

The toner composition is prepared as follows:
1. Methyl hydroxybenzoate and dipropylene glycol are mixed and heated to 80° C., stirred to dissolve uniformly.
2. Hydrolyzed sodium hyaluronate and butanediol are mixed uniformly.
3. *Betula alba* sap is heated to 80° C., and pentanediol and glycerol are added in sequence, stirred uniformly, and then the mixtures obtained in steps 1 and 2 are added.
4. The resultant is cooled down to 40° C., citric acid and arginine are added to adjust the pH, and discharged.

The toner shows excellent moisturizing, whitening and other skincare efficacy.

Example 4: Moisturizing Mask

The formulation of the moisturizing mask is shown in Table 5.

TABLE 5

| | |
|---|---|
| BETULA ALBA sap | 88.25 |
| Methyl hydroxybenzoate | 0.15 |
| Citric acid | 0.1 |
| Hydrolyzed sclerotium gum | 0.1 |
| Xanthan gum | 0.1 |
| Hydrolyzed sodium hyaluronate | 0.05 |
| Betaine | 2 |
| Glycerol | 4 |
| Butanediol | 4 |
| PEG/PPG-17/6 copolymer | 1 |
| Arginine | 0.2 |
| Bis(hydroxymethyl)imidazolidinyl urea | 0.05 |

The mask is prepared as follows:
1. Xanthan gum, hydrolyzed sclerotium gum, hydrolyzed sodium hyaluronate and glycerol are mixed uniformly.
2. Methyl hydroxybenzoate and butanediol are heated to 80° C. and dissolved until the solution is clear and transparent.
3. *Betula alba* sap (or water) is heated to 80° C., and citric acid, betaine and PEG/PPG-17/6 copolymer are added in sequence, stirred uniformly. The resultant is cooled down to 40° C., then the mixtures obtained in steps 1 and 2 are added, and bis(hydroxymethyl)imidazolidinyl urea is added.
4. Arginine is added to adjust the pH, and discharged.

Example 5: Moisturizing Lotion

The formulation of the moisturizing lotion is shown in Table 6.

TABLE 6

| | |
|---|---|
| BETULA ALBA sap | 74.7 |
| Methyl hydroxybenzoate | 0.2 |
| Citric acid | 0.1 |
| Xanthan gum | 0.1 |
| Hydrolyzed sodium hyaluronate | 1 |
| Glycerol | 8 |
| Dipropylene glycol | 3.05 |
| Acrylates/C10-30 alkyl acrylate crosspolymer | 0.1 |
| Propyl hydroxybenzoate | 0.1 |
| PEG-100 stearate, glyceryl stearate | 1 |
| C14-22 alcohol, C12-20 alkyl glucoside | 1 |
| Caprylic/capric triglyceride | 6 |
| BUTYROSPERMUM PARKII (Shea butter) | 1 |
| Cetyl alcohol | 1 |
| Polydimethylsiloxane | 2 |
| Arginine | 0.25 |
| Phenoxyethanol | 0.4 |

The moisturizing lotion is prepared as follows:

1. Oil phase: PEG-100 stearate, glyceryl stearate, C14-22 alcohol, C12-20 alkyl glucoside, caprylic/capric triglyceride, *Butyrospermum parkii* (Shea butter), cetyl alcohol, polydimethylsiloxane. The raw materials are heated to 80° C., dissolved and mixed uniformly.
2. Methyl hydroxybenroate, propyl hydroxybenroate and dipropylene glycol are heated to 80° C., dissolved and mixed uniformly.
3. Xanthan gum, hydrolyzed sodium hyaluronate, acrylates/C10-30 alkyl acrylate crosspolymer, and glycerol are mixed uniformly at room temperature.
4. Aqueous phase: *Betula alba* sap is heated to 80° C., the mixtures obtained in steps 2 and 3 are added; dissolved and mixed uniformly.
5. Emulsification: the aqueous phase and the oil phase are added to an emulsification pot, held at 60° C., homoemuisified for 5 mins at a speed of 3000 rpm, after the completion of the emulsification, arginine is added.
6. The resultant is stirred and cooled down to 40° C., phenoxyethanol is added, stirred uniformly, and discharged.

Example 6: Moisturizing Cream

The formulation of the moisturizing cream is shown in Table 7.

TABLE 7

| | |
|---|---|
| BETULA ALBA sap | 70.45 |
| Methyl hydroxybenzoate | 0.2 |
| Citric acid | 0.1 |
| Xanthan gum | 0.2 |
| Hydrolyzed sodium hyaluronate | 0.05 |
| Glycerol | 6 |
| Acrylates/C10-30 alkyl acrylate crosspolymer | 0.2 |
| Propyl hydroxybenzoate | 0.1 |
| Methyl glucose sesquistearate | 1 |
| PEG-20 methyl glucose sesquistearate | 2 |
| Caprylic/capric triglyceride | 6 |
| Glyceryl caprylate/caparate | 1 |
| Pentaerythrityl tetraethylhexanoate | 4 |
| BUTYROSPERMUM PARKII (Shea butter) | 3 |
| Cetyl alcohol | 3 |
| Polydimethylsiloxane | 2 |
| Arginine | 0.3 |
| Phenoxyethanol | 0.4 |

The moisturizing cream is prepared as follows:

1. Oil phase: methyl glucose sesquistearate, PEG-20 methyl glucose sesquistearate, caprylic/capric triglyceride, glyceryl caprylate/caparate, pentaerythrityl tetraethylhexanoate, *Butyrospermum parkii* (Shea butter), cetyl alcohol, polydimethylsiloxane. The raw materials are heated to 80° C., dissolved and mixed uniformly.
2. Methyl hydroxybenzoate, propyl hydroxybenzoate and phenoxyethanol are heated to 80° C., dissolved and mixed uniformly.
3. Xanthan gum, hydrolyzed sodium hyaluronate, acrylates/C10-30 alkyl acrylate crosspolymer, and glycerol are mixed uniformly at room temperature.
4. Aqueous phase: *Betula alba* sap is heated to 80° C., the mixture obtained in the above 3 is added, dissolved and mixed uniformly.
5. Emulsification: the aqueous phase and the oil phase are added to an emulsification pot, held at 80° C., homoemulsified for 5 mins at a speed of 3000 rpm, after the completion of the emulsification, arginine is added.
6. The resultant is stirred and cooled down to 40° C., the mixture obtained in the above 2 is added, stirred uniformly, and discharged.

Example 7: Moisturizing Face Cleanser

The formulation of the moisturizing face cleanser is shown in Table 8.

TABLE 8

| | |
|---|---|
| BETULA ALBA sap | 44.2 |
| Citric acid | 0.1 |
| Methyl hydroxybenzoate | 0.2 |
| Polyethylene glycol-14M | 0.1 |
| Hydrolyzed sodium hyaluronate | 0.5 |
| Propanediol | 24.5 |
| Sodium lauroyl glutamate | 22 |
| PEG-150 distearate | 3 |
| Cocamide MEA | 1 |
| Sodium cocoyl isethionate, stearate | 4 |
| Phenoxyethanol | 0.4 |

The face cleanser is prepared as follows:

1. *Betula alba* sap, citric acid, methyl hydroxybenzoate, polyethylene glycol-14M, hydrolyzed sodium hyaluronate, and propanediol are mixed uniformly and heated to 80° C.
2. The mixture is held at 80° C., and added with sodium lauroyl glutamate, PEG-150 distearate, cocamide MEA, sodium cocoyl isethionate, stearate in sequence, and held at the temperature with stirring until the mixture dissolved completely.
3. The resultant is cooled down with stirring to 35° C.
4. Phenoxyethanol is added and mixed uniformly, and discharged.

Example 8: Moisturizing Essence

The formulation of the moisturizing essence is shown in Table 9.

TABLE 9

| | |
|---|---|
| BETULA ALBA sap | 81.55 |
| Methyl hydroxybenzoate | 0.15 |
| Citric acid | 0.1 |
| Sodium poly-glutamate | 0.1 |
| Xanthan gum | 0.1 |
| Hydrolyzed sodium hyaluronate | 0.05 |

TABLE 9-continued

| | |
|---|---|
| Trehalose | 2 |
| Glycerol | 6 |
| 1,3-Propanediol | 5 |
| Acrylates/C10-30 alkyl acrylate crosspolymer | 0.2 |
| PPG-10 methyl glucose ether | 4 |
| Arginine | 0.35 |
| Phenoxyethanol | 0.4 |

The essence is prepared as follows:

1. Methyl hydroxybenzoate and phenoxyethanol are nixed and heated to 80° C., stirred and dissolved uniformly.

2. Xanthan gum, hydrolyzed sodium hyaluronate, acrylates/C10-30 alkyl acrylate crosspolymer and 1,3-propanediol are mixed uniformly.

3. *Betula alba* sap is heated to 80° C., added with citric acid, glycerol, sodium poly-glutamate, trehalose, PPG-10 methyl glucose ether in sequence, stirred uniformly, and then added to the mixture obtained in the above 2.

4. The resultant is stirred slowly and cooled down to 40° C., added with the mixture obtained in the above 1 and then added with arginine to adjust the pH, and discharged.

The technical solutions described in the examples are preferred embodiments of the invention, and various modifications and variations can be made without departing from the spirit of the invention, and such modifications and variations are also considered to be within the scope of the invention.

The invention claimed is:

1. A moisturizing cosmetic composition, comprising:
   (A) 30-99 wt % of birch sap,
   (B) 0.001-5 wt % of hydrolyzed sodium hyaluronate, and
   (C) optionally, ingredients commonly used in skin care cosmetics;
   wherein the percentage is based on the total weight of the composition, and
   the moisturizing cosmetic composition does not comprise water alone added as a separate component.

2. The moisturizing cosmetic composition according to claim 1, wherein the composition does not comprise a chelating agent.

3. The moisturizing cosmetic composition according to claim 1, wherein the composition comprises 50-95 wt % of birch sap.

4. The moisturizing cosmetic composition according to claim 1, wherein the composition comprises 0.01-1 wt % of hydrolyzed sodium hyaluronate.

5. The moisturizing cosmetic composition according to claim 1, wherein the hydrolyzed sodium hyaluronate has a molecular weight of 1-10 KDa.

6. The moisturizing cosmetic composition according to claim 2, wherein the composition comprises 50-95 wt % of birch sap.

7. The moisturizing cosmetic composition according to claim 2, wherein the composition comprises 0.01-1 wt % of hydrolyzed sodium hyaluronate.

8. The moisturizing cosmetic composition according to claim 2, wherein the hydrolyzed sodium hyaluronate has a molecular weight of 1-10 KDa.

9. A method for increasing the transdermal absorption rate of hydrolyzed sodium hyaluronate, comprising adding birch sap to a moisturizing cosmetic composition comprising hydrolyzed sodium hyaluronate but no water.

10. The method according to claim 9, wherein the composition comprises 30-99 wt % of birch sap and 0.001-5 wt % of hydrolyzed sodium hyaluronate, based on the total weight of the composition.

11. The method according to claim 9, wherein the composition does not comprise a chelating agent.

12. The method according to claim 9, wherein the hydrolyzed sodium hyaluronate has a molecular weight of 1-10 KDa.

13. The method according to claim 10, wherein the composition does not comprise a chelating agent.

14. The method according to claim 10, wherein the hydrolyzed sodium hyaluronate has a molecular weight of 1-10 KDa.

15. A moisturizing composition consisting of the following ingredients:
   *Betula alba* sap 70-90 (wt. %);
   methyl hydroxybenzoate 0.05-0.4 (wt. %);
   hydrolyzed sodium hyaluronate 0.1-0.5 (wt. %);
   pentanediol 1-5 (wt. %);
   glycerol 1-10 (wt. %);
   dipropylene glycol 0.5-5 (wt. %);
   butanediol 1-10 (wt. %);
   citric acid 0.01-0.5 (wt. %); and
   arginine 0.05-1 (wt. %).

16. The moisturizing composition according to claim 15, which is a toner.

* * * * *